(12) United States Patent
Koehler et al.

(10) Patent No.: US 9,940,540 B2
(45) Date of Patent: Apr. 10, 2018

(54) IMAGE CORRECTION DURING MAGNETIC RESONANCE DEPENDENT ON THE RECEPTION PROFILE OF THE RECEPTION ANTENNA

(71) Applicant: Siemens Aktiengesellschaft, Munich (DE)

(72) Inventors: Michael Koehler, Nuremberg (DE); Wilfried Landschuetz, Baiersdorf (DE); Juergen Nistler, Erlangen (DE); Markus Vester, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 162 days.

(21) Appl. No.: 14/970,846

(22) Filed: Dec. 16, 2015

(65) Prior Publication Data
US 2016/0171670 A1  Jun. 16, 2016

(30) Foreign Application Priority Data
Dec. 16, 2014 (DE) .......... 10 2014 226 034

(51) Int. Cl.
G06K 9/00 (2006.01)
G06K 9/52 (2006.01)
G01R 33/56 (2006.01)
A61B 5/055 (2006.01)
G01R 33/24 (2006.01)

(52) U.S. Cl.
CPC .......... *G06K 9/52* (2013.01); *G01R 33/5608* (2013.01); *A61B 5/055* (2013.01); *G01R 33/246* (2013.01)

(58) Field of Classification Search
None
See application file for complete search history.

(56) References Cited

U.S. PATENT DOCUMENTS

| | | | |
|---|---|---|---|
| 8,320,646 B2* | 11/2012 | Hu ..................... | G01R 33/4824 324/309 |
| 2003/0035574 A1 | 2/2003 | Kiefer et al. | |
| 2006/0106299 A1 | 5/2006 | Uchizono et al. | |
| 2008/0187196 A1* | 8/2008 | Hu ..................... | G01R 33/5611 382/128 |
| 2009/0224756 A1 | 9/2009 | Machida et al. | |
| 2009/0309594 A1* | 12/2009 | Feiweier ............. | G01R 33/288 324/309 |
| 2012/0019248 A1 | 1/2012 | Nonaka | |

(Continued)

OTHER PUBLICATIONS

Collins et.al: "Different Excitation and Reception Distributions With a Single-Loop Transmit-Receive Surface Coil Near a Head-Sized Spherical Phantom at 300 MHz",: Magnetic Resonance in Medicine, vol. 47, pp. 1026-1028, (2002).

(Continued)

*Primary Examiner* — Tahmina Ansari
(74) *Attorney, Agent, or Firm* — Schiff Hardin LLP

(57) ABSTRACT

In a method and apparatus for correcting image data acquired by an image data acquisition scanner of a magnetic resonance system, a reception profile of a reception antenna of the magnetic resonance scanner is determined. A correction function is determined by which an asymmetry of the reception profile with respect to a symmetry plane is corrected. Furthermore, image data are received and corrected by multiplying the intensity values of the image data with the determined correction function.

14 Claims, 5 Drawing Sheets

(56) References Cited

U.S. PATENT DOCUMENTS

| | | | |
|---|---|---|---|
| 2012/0032677 A1* | 2/2012 | Dannels | G01R 33/5659 |
| | | | 324/309 |
| 2014/0035575 A1 | 2/2014 | Kabasawa et al. | |
| 2015/0362577 A1* | 12/2015 | Nittka | G01R 33/56536 |
| | | | 324/309 |
| 2016/0171670 A1* | 6/2016 | Koehler | G06K 9/52 |
| | | | 382/131 |

OTHER PUBLICATIONS

Marques et al; "MP2Rage, A Self Bias-Field Corrected Sequence for Improved Segmentation and $T_1$-Mapping at High Field"; NeuroImage,; vol. 49; No. 2; pp. 1271-1281; (2010).

Van De Moortele et al., "$T_1$ Weighted Brain Images at 7 Tesla Unbiases for Proton Density $T_2$* Contrast and RF Coil Receive $B_1$ Sensitivity with Simultaneous Vessel Visualization," NeuroImage, vol. 46, pp. 432-436 (2009).

* cited by examiner

IMAGE CORRECTION DURING MAGNETIC RESONANCE DEPENDENT ON THE RECEPTION PROFILE OF THE RECEPTION ANTENNA

BACKGROUND OF THE INVENTION

Field of the Invention

The invention concerns a method for correcting image data acquired by operation of an image data acquisition scanner of a magnetic resonance system. The invention also concerns a method for magnetic resonance imaging of a region of an examination subject. The invention further concerns an image correction device for a magnetic resonance measurement. The invention also concerns a magnetic resonance system.

Description of the Prior Art

In a magnetic resonance system, the body that is to be examined is typically exposed to a relatively high basic magnetic field, for example of 1.5 tesla, 3 tesla or 7 tesla, with the use of a basic field magnet. After the basic field is applied, nuclei in the examination subject align themselves along the field because they have a non-zero nuclear magnetic dipole moment, called spin. This collective behavior of the spin system is described by the macroscopic "magnetization". The macroscopic magnetization is the vector sum of all of the microscopic magnetic moments in the object at a specific location. In addition to the basic field, a magnetic field gradient, by which the magnetic resonance frequency (Larmor frequency) at the respective location is determined, is applied by a gradient coil system. Radio-frequency excitation signals (RF pulses) are then emitted via a radio-frequency transmission system by one or more suitable antennas, with the intended goal of tipping the macroscopic magnetization through a defined flip angle in relation to the magnetic field lines of the basic magnetic field. When such an RF pulse acts on spins that have already been excited, these can be flipped (deflected) into a different angular position or even flipped back into an initial state parallel to the basic magnetic field. During the relaxation of the excited nuclear spins, radio-frequency signals, called magnetic resonance signals, are resonantly emitted, received (detected) by suitable reception antennas (also called magnetic resonance coils or reception coils). The received signals are subsequently demodulated and digitized, and then processed further as data referred to as "raw data". The acquisition of the magnetic resonance signals takes place in the spatial frequency domain, the so-called "k-space", the data entry points in k-space being traversed as a function of time along a "gradient trajectory" (also called "k-space trajectory") defined by the switching of the gradient pulses during a measurement e.g. of a slice. In addition, the RF pulses must be emitted in a coordinated manner as appropriate with respect to time. Following further processing steps, which usually are also dependent on the acquisition method, the desired image data is finally reconstructed from the thus acquired raw data by a two-dimensional Fourier transform. Alternatively, three-dimensional volumes can also be excited and read out in a defined manner in the interim, the raw data in turn being classified after further processing steps into a three-dimensional k-space. A three-dimensional image data volume can then be reconstructed accordingly by a three-dimensional Fourier transform.

In order to control a magnetic resonance tomography system during the measurement, it is common practice to use specific predefined pulse sequences, i.e. strings of defined RF pulses as well as gradient pulses in different directions and readout windows, during which time the reception antennas are switched to reception mode and the magnetic resonance signals are received and processed. Such sequences are parameterized in advance for a desired examination, for example a specific contrast of the calculated images, with the use of a scan specification known as a measurement protocol. The measurement protocol may also contain further control data for the measurement. In this regard there are a multiplicity of magnetic resonance sequence techniques in accordance with which pulse sequences may be constructed.

Particularly when high field strengths of 3 tesla or more are used in MR measurements, local variations in the radio-frequency field, also called the B1 field, can occur that are caused by electrical or dielectric effects. These variations can lead to inhomogeneities in the measured signal distribution, which has an influence on the quality of the reconstructed images acquired, and consequently have an impact on the diagnostic quality. Such variations are generally dependent on the shape and nature of the object being examined, for which reason different variations in the B1 field may be observed in different patients and in different regions of the body.

In this connection, the relevant effects can be subdivided into two categories: Firstly, a variation in the B1 field present in the transmit case causes an inhomogeneous distribution of the achieved flip angles. Phenomena associated therewith are referred to in the following as TX effects. Secondly, local variations in the reception sensitivity of reception coils are also observed, even in the case of such reception coils which are configured as volume coils. The phenomena associated therewith are referred to in the following as RX effects and owing to the reciprocity principle known in MR imaging are also linked with variations in the B1 field.

The symmetry of parts of the body is taken into account in many clinical diagnostic questions. This is the case, for example, in many examinations in the head region. In this regard an asymmetric signal distribution, and consequently an asymmetry in the reconstructed MR image (e.g. in relation to front/back or left/right), may point to a medical disorder. If asymmetric signal distributions are brought about by the above-described TX or RX effects, this can lead to a false indication of a medical disorder, or at least have a negative effect on the image quality.

In transverse head examinations, for example, a disruptive signal overshoot may occur in the right-hand half of the image even though the head is relatively symmetrical (referred to the central sagittal plane) and for that reason the clinical observer would also expect symmetrical images.

Local coils (or surface coils) can exhibit significantly inhomogeneous reception profiles. As used herein, a reception profile, also referred to in abbreviated form as RX profile, means the intensity of the reception signals as a function of their place of origin in the case of a homogeneous distribution of the tissue properties (such as proton density and relaxation times), as well as in the case of homogeneous distribution of the basic magnetic field and the flip angle.

Conventionally, therefore, the images (after the signals of the individual local coil elements have been combined by a suitable method) are frequently either smoothed by an image-based filter, or are normalized to the relatively homogeneous signal of a volume coil, e.g. the body coil present in whole-body scanners. However, the above-described RX effects result in the signal of the volume coil no longer being homogeneous under certain conditions and therefore having an impact on the local coil images.

The cited use of image filters in some cases likewise proves unsatisfactory, e.g. the entire image impression can be distorted as a result and pathological effects on the image can be influenced under certain conditions.

During the acquisition of measured signals, the reception profile RP(x,y,z) of the reception coil combination used, or of the coil combination to which the measured signal is normalized (the body coil in the above example), is incorporated proportionally into the signal S(x,y,z) measured at the location x,y,z:

$$S(x,y,z) \propto RP(x,y,z) \qquad (1)$$

The effect of the TX profile, which determines the flip angle actually present at the location (x,y,z) during the alignment of the spins relative to the orientation of the magnetic field lines of the basic magnetic field, on the measured signal is considerably more complicated and in general is dependent on the sequence characteristics (e.g. type of sequence, echo time and repetition time) as well as on the properties of the tissue being examined (such as proton density and relaxation times).

As already mentioned, one possibility of compensating for the changed signal distribution is the use of image filters, with the intended object of improving the homogeneity of the MR image acquisitions. This measure is therefore aimed at compensating for the combined impact of the described TX and RX effects. Filters of the type can be designed e.g. to remove low-frequency intensity variations in the spatial domain from the images. These "slowly varying" components are different from the anatomic structures, which generally are composed of higher spatial frequencies. Some image filters exploit the fact that the same signal intensity should be present in specific image regions located at different positions. If a difference in signal intensity is present, then an inhomogeneity in the transmit/reception behavior of the arrangement may be inferred and the inhomogeneity can be corrected accordingly.

Some methods that are used address only the TX effects, e.g. the use of B1 shimming or other pTX methods in order to achieve a homogeneous distribution of the flip angles. These methods assume the presence of a number of transmit channels. In B1 shimming, a suitable polarization is chosen in this case through suitable selection of the amplitude ratios and phase differences between the different transmit channels, the polarization leading to the smallest possible variations in the achieved flip angles. However, in some cases a large number (e.g. 8 or more) of transmit channels are necessary in order to achieve a satisfactory homogeneity. Such an arrangement is quite expensive and usually not available in commercial systems.

Alternatively, it is also possible to use B1-insensitive RF pulses in order to compensate for the TX effects. Disadvantageous aspects with this approach, however, are the longer pulse duration and the increased energy dose, for which reason this approach is not suitable for all MR sequences.

SUMMARY OF THE INVENTION

An object of the present invention is to provide an easy-to-implement but nonetheless effective method for correcting the described inhomogeneity in the reception behavior of magnetic resonance systems.

In the inventive method for correcting image data acquired by means of an image data acquisition scanner of a magnetic resonance apparatus, a reception profile of a first reception antenna of the magnetic resonance scanner is determined prior to the acquisition of diagnostic data from a patient. In this case the reception antenna can be either the antenna with which the diagnostic image acquisition will be performed subsequently, or a different reception antenna to which the reception antenna with which the later image acquisition will be performed is normalized. On the basis of the determined reception profile, a correction function is then determined with which an asymmetry of the reception profile with respect to a symmetry plane can be corrected. The symmetry plane can be, for example, a symmetry plane of a region of interest that is to be examined, for example a part of the body, such as the head. During the diagnostic image acquisition, image data are received for example via an image data interface which receives the image data from the reconstruction computer of the magnetic resonance apparatus, for example, and corrects the image data by multiplying the intensity values of the image data with the determined correction function. It may also be the case that data relating to the reception profile and image data are already present in a memory and within the scope of the described method, such data are forwarded via the image data interface to the image correction computer and corrected thereby.

The correction of the asymmetry of the acquired image of a region that is to be examined is made based on information that the region that is to be examined is symmetrical with respect to a specific symmetry plane. The correction advantageously eliminates only asymmetries caused by the asymmetry of the reception profile, while true asymmetries that are caused by a medical disorder or a pathological process are retained unchanged. Pathologies can lead e.g. to local variations in the relaxation times, as a result of which the measured signal changes at the sites of the pathologies. However, these effects are independent of the shape of the RX profile. The latter can be modified e.g. by eddy currents induced in the body, but not by local variations in the relaxation times. Accordingly, pathologies generally lead to a modified signal without the RX profile being affected at these sites.

The described method is particularly suitable for measurements in regions of the body which are symmetrical and in that for that reason symmetric signal distributions are also to be expected, such as is the case in the brain.

Because the correction advantageously takes place in a pure post-processing step, the diagnostic imaging measurement is not affected. There is therefore no need to modify the diagnostic imaging as such in comparison with existing measurement methods. For this reason, there is no increase in the actual measurement time. Only the time for the measurement of the data from which the reception profile is determined must be invested in addition. It may be possible, however, to perform the measurement for acquiring the reception profile at a lower resolution than the actual image acquisition.

In the method according to the invention for magnetic resonance imaging of a region of an examination subject that is to be imaged, a homogeneous basic field $B_0$ is first generated in the region that is to be imaged. In addition, a time-dependent and space-dependent gradient field is also generated in the region that is to be imaged. Furthermore, an excitation field is generated on the basis of a pulse sequence and used to generate echo signals which include structural information relating to the region that is to be imaged. These echo signals are acquired as RF reception signals from the region that is to be imaged of the object that is to be imaged. Raw data is generated from the acquired RF reception signals and image data is reconstructed on the basis of the raw data. The method according to the invention for correcting image data acquired by an image data acquisition scanner of a magnetic resonance apparatus is applied to the reconstructed image data.

The image correction computer according to the invention has a reception profile determination stage or module (processor) which is configured to determine the reception profile of a reception device of the magnetic resonance scanner. Prior to an acquisition of images of a particular patient, for example, the reception profile determination module determines a type of test image from which the reception profile assigned to a specific region of a specific patient is determined. The image correction computer according to the invention additionally has a correction function determination module, which is configured to determine a correction function with which an asymmetry of the reception profile with respect to a symmetry plane is corrected. The image correction computer according to the invention furthermore has an image data interface which is configured for acquiring image data. The image data can be received from an image data reconstruction computer during a measurement or after a measurement, for example. The image correction device according to the invention also has an image data correction module, which is configured to correct the received image data by multiplying the intensity values of the image data with the determined correction function.

The magnetic resonance apparatus according to the invention includes the image correction computer according to the invention. The image correction computer according to the invention is therefore part of the magnetic resonance apparatus. The computer may, for example, be part of an existing control computer, reconstruction computer or evaluation computer.

The (cited and, where appropriate, further) units are not necessarily required to be embodied as hardware components, but can also be implemented as software modules, for example when the described functions can be executed by another component already implemented on the same device, such as a central processing unit or an already existing control computer, for example. Equally, the cited units may be formed by hardware and software components, such as a standard hardware unit that is specifically configured for the actual intended application by means of software, for example. Moreover, a number of units may also be combined in a common unit.

The invention also encompasses a non-transitory, computer-readable data storage medium that can be loaded directly into a processor of the magnetic resonance apparatus and that is encoded with a program code that causes all of the steps of the method according to the invention (including according to the aspects described further below) to be performed when the program code is executed by the magnetic resonance apparatus under the control of the processor.

In a preferred embodiment of the method according to the invention, the first reception antenna is a volume coil to which the reception profile of a local coil is normalized. In the method, the image data are generated from reception signals detected by the local coil. In this embodiment, the volume coil can have a relatively homogeneous reception signal. In this case, therefore, the correction of the reception profile of the volume coil can prove considerably less demanding. The local coil that is then used to perform the diagnostic image acquisition is normalized to the volume coil, i.e. the behavior of the local coil corresponds to a behavior of the reference coil when in the latter different channels are combined with specific weights. This combination must be taken into consideration in the determination of the reception profile.

In another special embodiment of the method according to the invention, the symmetry plane is the yz plane or the xy plane or the xz plane (see FIG. 1). Typically, during the acquisition of MR images of a patient, there exists a symmetry with respect to the yz plane. For example, the head in common with other regions of the body possesses a symmetry with respect to the sagittal plane. Because only the asymmetry of the reception profile with respect to a chosen plane is corrected, the original image impression familiar in medical application remains largely unchanged. Alternatively, it may also be the case that the symmetry plane can also lie somehow askew, when, for example, the head is inclined relative to the rest of the body or the scanner.

In a preferred embodiment of the method according to the invention, the symmetry plane is determined by an automatic method. In this case a pattern recognition algorithm automatically detects the shape of the part of the body just examined and as a result also finds the symmetry plane (or the central plane with respect to a defined direction). For example, there are methods (called "auto align" in the case of Siemens scanners) that recognize the shape for a chosen part of the body and center the examined volume automatically around the relevant part of the body (e.g. the head) of the patient. If the head is, e.g., inclined, this is recognized by this method. As soon as the acquisition volume is centered around the part of the body in question and aligned accordingly, the symmetry plane (or the central plane) can thus also be determined directly.

Preferably, the correction function is a square root of a quotient from the reception profile mirrored at the symmetry plane, and the reception profile. Such a correction function symmetrizes the reception profile of the reception coil and in addition ensures that the corrected reception profile is identical to the uncorrected reception profile in the symmetry plane. A further advantage of the correction function according to the invention is that with this function, only the asymmetric RX components are corrected. In many cases—even without the use of a correction—a decrease in the signal intensities with distance from the ordinate axis is used in order to correct an inhomogeneous distribution of the TX profile (or transmit profile, or RF transmit field). This is because in many cases (e.g., in the head at a basic magnetic field strength of 3 tesla) the intensity of the distribution of the TX profile is likewise stronger toward the symmetry axis and decreases toward the exterior. Such an overshoot in the center brings about a corresponding overshoot of the flip angle in this area. Since an increase in the flip angle relative to the actual target flip angle leads in some imaging measurements to a sinking signal. In these sequences, due to the overshoot of the reception profile in the center and due to the overshoot of the TX profile in the center, a reciprocal compensation of the two overshoots of the TX profile and of the RX profile occurs.

For example, as a result of the inventive correction, the variation in the signal intensity from the image center to the outer area is not significantly affected in these measurements in the head region. The image impression would be affected if the measured image were to be corrected completely by the reception profile if, for example, the image were to be divided by the reception profile of the reception antenna and no correction of the TX effects were to be carried out. In that case a decline in the signal would result from the outer area toward the center in measurements in the head region, since the uncorrected reception profile has a strong overshoot in the center and the echo signal is correspondingly weaker in the center, as has already been explained.

In an embodiment of the method according to the invention for correcting image data acquired by an image data acquisition scanner of a magnetic resonance apparatus, determining the reception profile can be done by determining a transmit profile and mirroring the transmit profile at a symmetry plane. This embodiment of the method according to the invention makes use of the fact that the reception sensitivity of a coil corresponds to the transmit profile mirrored at the symmetry plane. A B1 mapping method can be used, for example, in order to determine the transmit profile.

This approach is explained at length in the publication by Collins, C. M., et al. titled "Different excitation and reception distributions with a single-loop transmit-reception surface coil near a head-sized spherical phantom at 300 MHz", Magnetic Resonance in Medicine 47 (2002): pp. 1026-1028.

In addition to the correction of the reception profile, an inhomogeneity of the transmit profile can be corrected during the correction of the image data. In this case the already cited methods can be employed, e.g. the use of B1 shimming or other pTX methods in order to achieve a homogeneous distribution of the flip angles.

The correction of the inhomogeneity of the transmit profile can include multiplying the intensity values of the image data with an additional correction function.

In the method according to the invention for magnetic resonance imaging, a pulse sequence containing B1-insensitive RF pulses can be used as the RF pulse sequence. By using such a special pulse sequence it is possible to reduce artifacts that are generated due to an inhomogeneous distribution of the B1 field.

DESCRIPTION OF THE PREFERRED EMBODIMENTS

Figure 1:
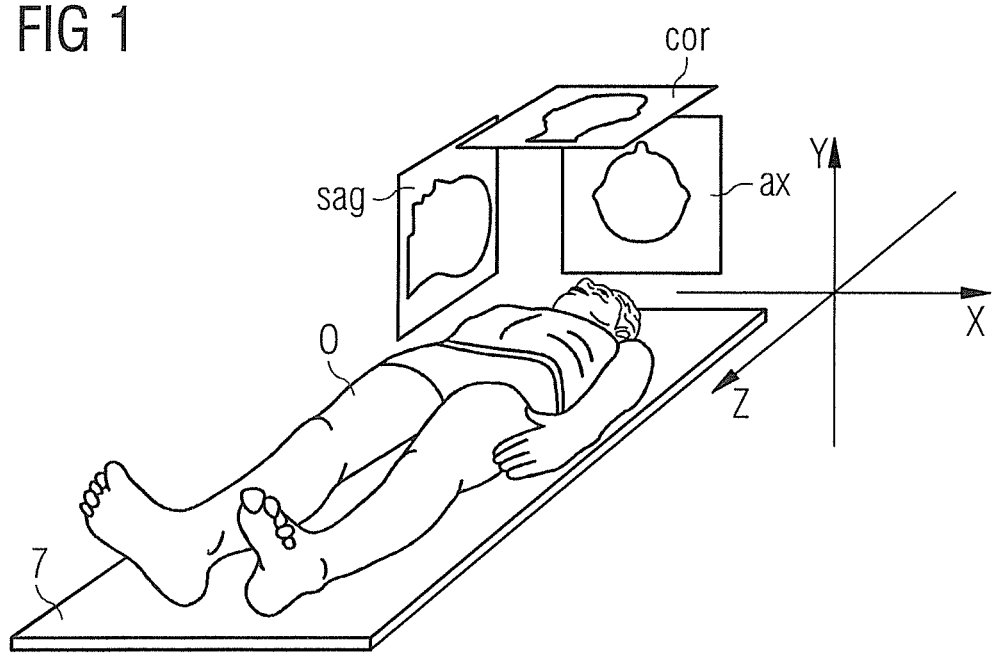
FIG. 1 schematically shows a typical orientation of a patient in a magnetic resonance system.

FIG. 1 shows the orientation of a coordinate system of a magnetic resonance system comprising x-axis, y-axis and z-axis. A patient O lying on a patient table is positioned oriented in the z-direction with respect to the patient's longitudinal axis. Also shown as an example in FIG. 1 are sectional images (slices) of the head of the patient O that represent scans performed in the sagittal plane sag (yz plane), the coronal plane cor (xz plane) and parallel to the axial plane ax (xy plane). In this context it is particularly of advantage, due to the symmetry of the head, for the reception profile in the reference case to be identical in the coronal plane or parallel to the coronal plane for regions of identical tissue to the left and right of the mid-sagittal plane. This is because asymmetries with respect to the mid-sagittal plane can then be interpreted as an indication of medical disorders.

In order to obtain a symmetric distribution of the signal intensity in the reference case, i.e. in a case based on a healthy patient, the reception profile of the reception coil used to receive measured signals is taken into account according to the invention in order to correct the acquired measured signals as a function of the location from which they were emitted. It is also similarly advantageous if the reception profile is identical in the axial plane or parallel to the axial plane for regions of identical tissue to the left and right of the mid-sagittal plane. This is because in this orientation the brain is likewise symmetrical with respect to the mid-sagittal plane.

Figure 2:
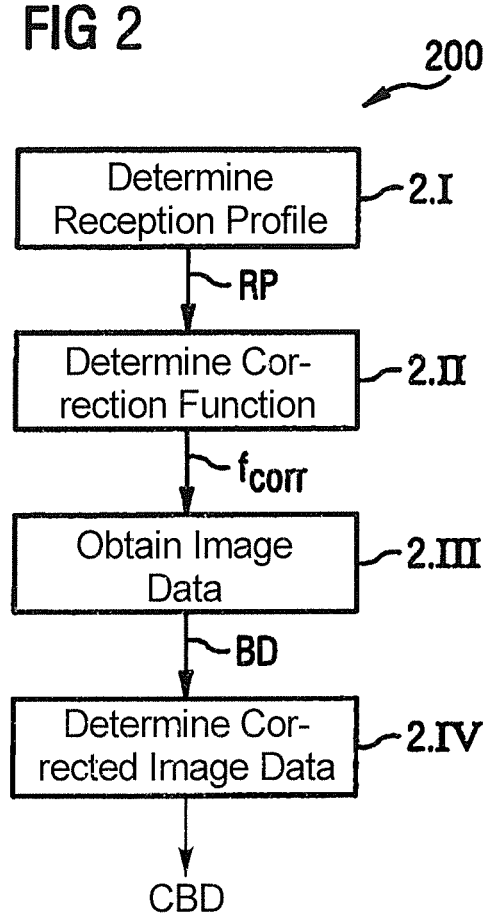
FIG. 2 is a flowchart illustrating a method according to an exemplary embodiment of the invention.

FIG. 2 schematically illustrates the workflow of a method 200 for correcting image data acquired by the image data acquisition scanner of a magnetic resonance system. In step 2.I, a reception profile RP that represents the reception profile a reception antenna arrangement of the magnetic resonance scanner is determined. This reception profile RP does not necessarily have to be the reception profile of the reception antenna with which the diagnostic image acquisition will be performed subsequently. For example, the determined reception profile can be the reception profile of a volume coil, or the reception profile of a local coil or a group of local coils, with which the diagnostic scan of a region of a patient that is to be examined, is normalized. An electronic designation (description) of the representative reception profile RP is provided to a computer.

As already mentioned, the reception profile can therefore be the transmit profile TP mirrored at the symmetry plane, i.e. the central sagittal plane of the patient being examined. The transmit profile can in turn be determined with the use of a known B1 mapping method.

In step 2.II, a correction function $f_{corr}$ is determined in the computer by which an asymmetry of the reception profile RP with respect to a symmetry plane, in this case the yz plane (see FIG. 1), is corrected. The correction function can have in particular the following form:

$$f_{corr}(x, y, z) = \sqrt{\frac{RP(-x, y, z)}{RP(x, y, z)}} \quad (2)$$

wherein RP(x,y,z) denotes the reception profile effective at the location (x,y,z). The correction function $f_{corr}$ is therefore chosen such that a compensation of an asymmetry with respect to the symmetry plane of the examination subject, in this case the yz plane, which was caused by an asymmetry of the representative reception profile RP, is achieved and furthermore the corrected signal is not distorted with respect to its intensity averaged over the x-axis (see FIG. 3). The coordinates used (x,y,z) can be, for example, coordinates of the patient coordinate system, in which case they therefore correspond to the coordinates (sag,cor,tra) or (left, anterior, caudal).

In another embodiment, a correction of the reception profile RP with respect to the xz plane or the mid-coronal plane may also be beneficial, when such symmetry exists in the body part under examination. For example, certain internal organs may be symmetrical with respect to such a plane or planes. In such a case the correction function is expressed as follows:

$$f_{corr}(x, y, z) = \sqrt{\frac{RP(x, -y, z)}{RP(x, y, z)}} \quad (2^*)$$

In step 2.III, image data BD are obtained from the examination subject by acquiring raw magnetic resonance data from the subject with the use of the image data acquisition scanner and reconstructing the image data BD from the raw data in a known manner. The reconstructed image data BD are still distorted due to the asymmetric reception profile or containing artifacts.

In step 2.IV, finally, corrected image data CBD are determined by multiplying the intensity values of the image data BD with the determined correction function:

$$S_{corr}(x,y,z) = S(x,y,z) \cdot F_{corr}(x,y,z) \quad (3)$$

wherein $S_{corr}$ is the corrected measured signal in the spatial domain and $S(x,y,z)$ is the received measured signal, corrupted due to the above-described inhomogeneities, which corresponds to an intensity of a pixel or voxel at the location $(x,y,z)$.

Figure 3:
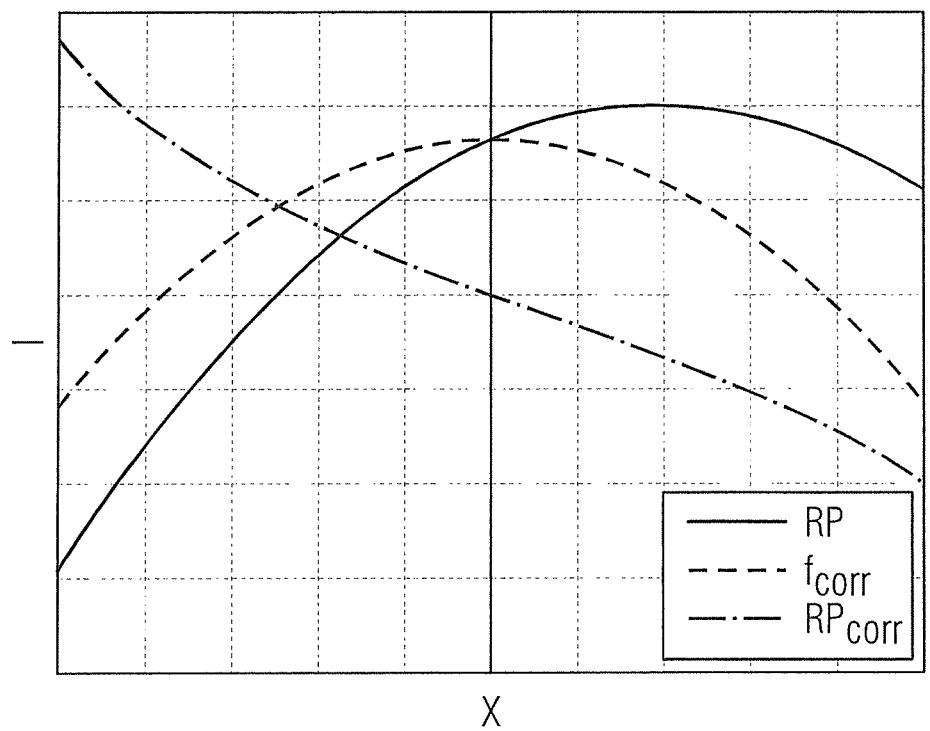
FIG. 3 shows a graph in which the correction of an asymmetric reception profile is illustrated.

FIG. 3 is a graph illustrating the effectiveness of the correction performed with the method described in FIG. 2. The intensity I assigned to an uncorrected reception profile RP is shown as a function of the position x in arbitrary units as a solid line, the yz plane, i.e. the central sagittal plane or a projection thereof, being drawn in as the ordinate axis. It is noticeable that not only is the reception profile RP asymmetric with respect to the ordinate axis, but also its values decrease with increasing distance from the maximum of the reception profile (i.e. to the right of x=0). Also shown, as a dot-dash line is a correction function $f_{corr}(x)$, as is determined by the method 200 illustrated in FIG. 2. Finally, the corrected reception profile $RP_{corr}$ is also plotted by dashed lines. In this case the reception profile is yielded as follows:

$$RP_{corr}(x) = f_{corr}(x) \cdot RP(x) \quad (4)$$

As can be seen, the corrected reception profile is symmetric and furthermore has a maximum at the symmetry axis. This property of the corrected reception profile can be used to compensate for an attenuation of the signal near to the ordinate axis due to an overshoot of the transmit profile in this area. An overshoot of the transmit profile TP can therefore be corrected by an overshoot of the reception profile RP. This additional compensation effect occurs in measurements in which an increase in the flip angle (relative to the target flip angle) results in a decrease in the signal. However, it is not the case in all parts of the body that the reception profile and the transmit profile increase in the center of the object. The cited effect occurs, for example, in head measurements at 3 tesla, but not necessarily in hip measurements, for example.

Figure 4:
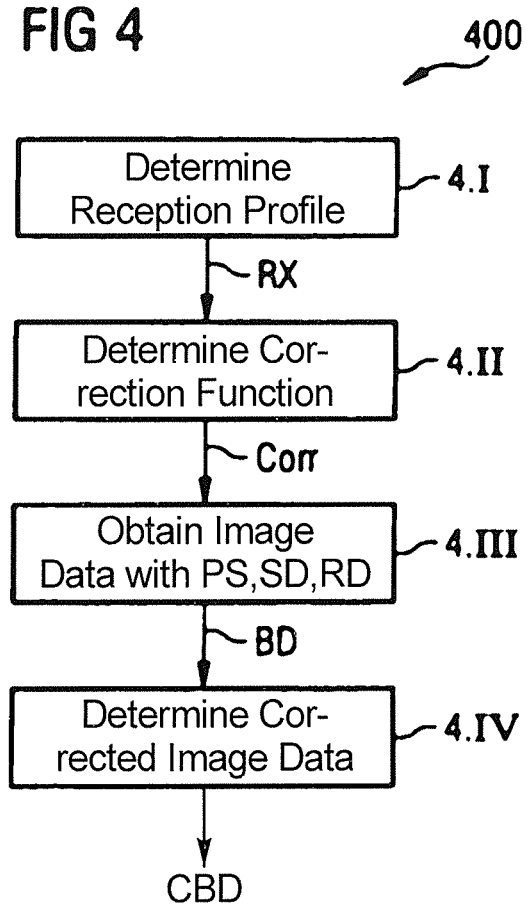
FIG. 4 is a flowchart illustrating a method according to an exemplary embodiment of the invention.

FIG. 4 shows a method 400 for magnetic resonance imaging of a region of interest ROI of an examination subject O that is to be imaged according to an exemplary embodiment of the invention. In step 4.I, analogously to step 2.I, a reception profile of a coil array is determined in the first instance. At step 4.II, analogously to step 2.II, a correction function $f_{corr}$ is determined with which an asymmetry of the reception profile RP with respect to a symmetry plane is corrected. In step 4.III, the actual image acquisition is performed with the use of a magnetic resonance measurement. In such an MR measurement, a homogeneous basic field $B_0$ is typically generated in the region ROI that is to be imaged. In addition, a time-dependent and space-dependent gradient field $G(r,t)$ is usually generated in the region ROI that is to be imaged. Finally, for example, an RF excitation field $B_1$ is generated on the basis of an RF pulse sequence PS, by which an excitation or alignment of nuclear spins by a specific flip angle is achieved. The subsequently relaxing magnetic moments are excited for example with the use of a refocusing pulse which is part of the pulse sequence PS in order to emit an RF echo signal S. This refocusing pulse can be for example an RF pulse or a gradient pulse. Echo signals SD, which contain image information relating to the region of interest ROI that is to be imaged of the object O that is to be imaged, are subsequently detected by reception antennas. Raw data RD are also generated in such a measurement on the basis of the acquired signals SD. In this step, the acquired signals SD are digitized. Finally, image data BD are generated on the basis of the generated raw data RD. The image data BD are generated by a Fourier transform of the raw data RD generated in k-space into the image or spatial domain. In step 4.IV, finally, the image data BD is corrected to yield corrected image data CBD by multiplying the space-dependent intensity values assigned to the image data BD with the described correction function $f_{corr}$. The image data BD are made available in electronic form as a data file, such as for display at a monitor.

Figure 5:
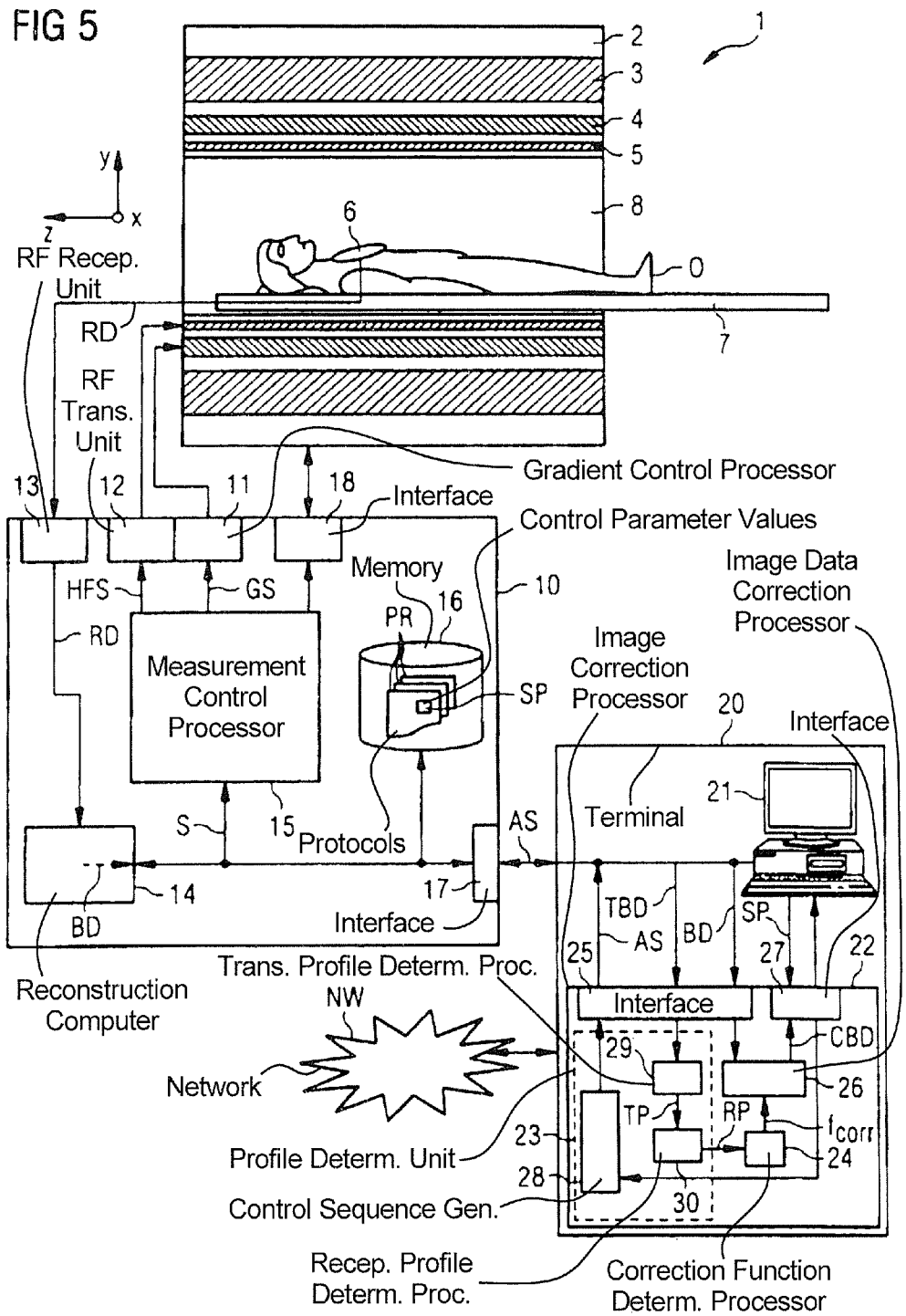
FIG. 5 schematically illustrates a magnetic resonance system according to an exemplary embodiment of the invention.

FIG. 5 shows a magnetic resonance apparatus 1 according to an exemplary embodiment of the invention. The apparatus 1 has the actual magnetic resonance scanner 2 with an examination chamber 8 or patient tunnel located therein. A bed 7 can be introduced into the patient tunnel 8 so that a patient O or test subject lying thereon can be positioned and supported at a specific position inside the magnetic resonance scanner 2 relative to the magnet system and radio-frequency system arranged therein during an examination or can also be moved between different positions during a measurement.

In this arrangement, the components of the magnetic resonance scanner 2 include a basic field magnet 3, a gradient system 4 having magnetic field gradient coils for generating magnetic field gradients in the x-, y- and z-directions, as well as a whole-body radio-frequency coil 5. The magnetic field gradient coils in the x-, y- and z-directions (spatial coordinate system) can be driven independently of one another, such that by a predefined combination, it is possible to apply gradients in any spatial directions, for example in a slice selection direction, in a phase encoding direction or in a readout direction, which are not necessarily parallel to the axes of the space coordinate system. Magnetic resonance signals induced in the examination subject O can be received via the whole-body coil 5, which usually serves also for emitting the radio-frequency signals in order to induce the magnetic resonance signals. Typically, however, these signals are received by a local coil array 6 composed, for example, of local coils (only one of which is shown in this case) placed on or under the patient O. All of these components are known in principle to the person skilled in the art and therefore are depicted only in schematic form in FIG. 5.

The components of the magnetic resonance scanner 2 can be activated by a control computer 10. This can be composed of a number of individual computers or processors (which may be spatially separated and connected to one another via suitable cables or the like). The control computer 10 is connected via a terminal interface 17 to a terminal 20 via which an operator can control the entire system 1. In the present case the terminal 20 has a computer 21 equipped with a keyboard, one or more monitors and further input devices, such as a mouse or the like, for example, or is embodied as such a computer 21 so that a graphical user interface is available to the operator.

The control computer 10 includes, among other components, a gradient control processor 11 which can in turn be formed of a number of subcomponents. Control signals are applied via the gradient control processor 11 to switch the individual gradient coils in accordance with a gradient pulse sequence GS. As described above, these are gradient pulses which are set at precisely predefined positions in time and with a precisely predefined time characteristic during a measurement.

The control computer 10 additionally includes a radio-frequency transmit unit 12 in order to inject radio-frequency pulses into the whole-body radio-frequency coil 5 in accordance with a predefined radio-frequency pulse sequence HFS of the control sequence AS. The radio-frequency pulse sequence HFS includes the aforementioned excitation pulses. The magnetic resonance signals are then received with the use of the local coil array 6, and the raw data RD received thereby is read out and processed by an RF reception unit 13. Following demodulation and digitization, the magnetic resonance signals are passed in digital form as raw data RD to a reconstruction computer 14, which reconstructs the image data BD from the raw data and stores the image data in a memory 16 and/or passes the data via the interface 17 to the terminal 20 so that it can be viewed by the operator. The image data BD can also be stored at other locations via a network NW and/or be displayed and evaluated. Alternatively, a radio-frequency pulse sequence can also be transmitted via the local coil array and/or the magnetic resonance signals can be received by the whole-body radio-frequency coil (not shown).

A further interface 18 is provided for conveying control commands to other components of the magnetic resonance scanner 2, such as e.g. the bed 7 or the basic field magnet 3, or for receiving measured values or other information.

The gradient control processor 11, the RF transmit unit 12 and the RF reception unit 13 are in each case activated in a coordinated manner by a measurement control processor 15. The latter ensures by appropriate commands that the desired gradient pulse sequence GS and radio-frequency pulse sequence HFS of the control sequence AS are transmitted. Provision must also be made to ensure that the magnetic resonance signals are read out at the local coils of the local coil array 6 at the appropriate time by the RF reception unit 13 and processed further, i.e. readout windows must be set by e.g. switching the ADCs of the RF reception unit 13 to reception mode. The measurement control processor 15 also controls the interface 18.

However, the basic workflow of such a magnetic resonance measurement and the cited control and driver components are known to those skilled in the art, so they need not be discussed in further detail herein. Moreover, such a magnetic resonance scanner 1 and the associated control computer 10 may also include a number of further components, which likewise need not be explained in detail herein. It is noted that the magnetic resonance scanner 2 may also be of different design, having, for example, a patient chamber that is open at the side, or being implemented as a smaller scanner in which only a part of the body can be positioned.

In order to start a measurement, an operator typically selects, via the terminal 20, a control protocol PR provided for that measurement from a memory 16 in which a number of control protocols PR for different measurements are stored. This control protocol PR includes, among other settings, various control parameter values SP for the respective measurement. The control parameter values SP include e.g. the type of sequence, the target magnetizations for the individual radio-frequency pulses, echo times, repetition times, the different selection directions, etc.

Moreover, instead of accessing the memory 16, the operator can also download control protocols via a network NW, for example from a manufacturer of the magnetic resonance system, said control protocols having corresponding control parameter values SP, and then utilize these as described below.

All of these control parameter values SP are made available inter alia via a first interface 27 to an image correction processor 22 so that the latter will first generate a suitable control sequence AS for carrying out the method according to the invention. The image correction processor 22 has a profile determination unit 23 having a control sequence generator 28 that generates a control sequence AS. The control sequence AS can include a first subsequence for generating test image data TBD which is used for determining a B1 map. The test image data are generated before or after the actual image acquisition. In addition, the profile determination unit 23 has a transmission profile determination processor 29, which determines a transmit profile TP on the basis of the generated test image data. The profile determination unit 23 further has a reception profile determination processor 30 which determines a reception profile RP on the basis of the determined transmit profile TP. The reception profile can also be stored in the memory 16 or in the computer 21 and be reused for subsequent measurements of the same examination subject O.

In principle it is also conceivable for a simulated or calculated reception profile to be used for the correction. In this case there would therefore be no need for an additional measurement (such as e.g. a B1 map measurement) in order to determine the reception profile therefrom.

The reception profile is subsequently forwarded to a correction function determination processor 24 which determines a correction function $f_{corr}$ according to equation (2) on the basis of the determined reception profile RP.

The image correction processor 22 furthermore has an interface 25 via which data AS for controlling the magnetic resonance system is transmitted and image data BD, TBD is received. The control sequence AS also includes a second subsequence which serves for the actual acquisition of images of a subregion of an examination subject. The image data BD received via the data interface 25 during the measurement is forwarded to an image data correction unit 26. Using the correction function $f_{corr}$, said image data correction processor 26 determines, from the received image data BD, corrected image data CBD which is forwarded for example via the interface 27 to the computer 21 and processed further by the latter and displayed, for example.

The entire image correction processor 22 and its components can be implemented on one or more suitable processors for example in the form of software by which the method according to the invention can be carried out.

The method and system described in detail herein are exemplary embodiments and the basic principle can also be varied in a multiplicity of different ways by those skilled in the art without departing from the scope of the invention. Thus, the image correction processor 22, for example, could be implemented as part of the control computer 10 or on the computer 21 instead of in the terminal, or on a separate computing system which is connected to the magnetic resonance system 1 via the network NW, for example. The directions can also be disposed arbitrarily in space, i.e. the x- and y-directions could be transposed, for example. The term "unit" does not preclude the possibility that a unit have multiple components that may be spatially distributed.

We claim as our invention:

1. A method for correcting magnetic resonance image data, comprising:
   providing a computer with an electronic designation of a representative reception profile that represents a reception profile of a reception antenna arrangement of a magnetic resonance scanner;
   in said computer, determining a correction function that corrects an asymmetry of said representative reception profile with respect to a symmetry plane of an examination subject from whom magnetic resonance raw data will be acquired with said magnetic resonance scanner;
   operating the magnetic resonance scanner to acquire magnetic resonance raw data from the examination subject;
   in said computer, applying a reconstruction algorithm to said raw data to reconstruct image data therefrom, said image data comprising intensity values that are distorted due to said asymmetry of the representative reception profile with respect to said symmetry plane of the examination subject; and
   in said computer, specifically correcting said distortion of said intensity values of said image data caused by the representative reception profile being asymmetric with respect to the symmetry plane of the examination subject, by multiplying the intensity values of the image data with said correction function, and thereby obtaining corrected image data, and making the corrected image data available from the computer in electronic form as a data file.

2. A method as claimed in claim 1 wherein said reception antenna arrangement comprises a volume coil and a local coil, and wherein said representative reception profile is a reception profile of said volume coil, and comprising acquiring said raw data from the examination subject with said local coil, and normalizing a reception profile of said local coil to the reception profile of said volume coil.

3. A method as claimed in claim 1 wherein said symmetry plane is at least one plane in a Cartesian coordinate system, said at least one plane being selected from the group consisting of the yz plane, the xy plane and the xz plane.

4. A method as claimed in claim 1 comprising automatically determining said symmetry plane in said computer by applying a pattern recognition algorithm to identify a shape of a selected body part of the examination subject and determining said symmetry plane from the shape of the body part.

5. A method as claimed in claim 4 comprising, dependent on the identified shape of the body part, automatically controlling said magnetic resonance scanner from said computer to automatically center, with respect to the body part, an examination volume from which said raw data are acquired.

6. A method as claimed in claim 1 wherein said correction function is the square root of a quotient of the representative reception profile mirrored at said symmetry plane, and said representative reception profile.

7. A method as claimed in claim 1 wherein said magnetic resonance scanner comprises a transmit antenna, and determining said representative reception profile of said reception antenna arrangement by mirroring a transmit profile of said transmit antenna with respect to a symmetry plane of the transmit antenna.

8. A method as claimed in claim 7 wherein said transmit antenna radiates a B1 field when said magnetic resonance scanner is operated to acquire said raw data, and comprising determining said transmit profile using a B1 mapping method.

9. A method as claimed in claim 7 wherein said transmit profile exhibits an inhomogeneity, and, in said computer, correcting said image data to correct a further distortion in said image data that results from said inhomogeneity of the transmit profile, in addition to correcting the distortion that occurs due to said asymmetry.

10. A method as claimed in claim 9 comprising correcting said further distortion in said image data by generating a further correction function that corrects for said inhomogeneity, and multiplying the intensity values of the image data with said further correction function.

11. A method as claimed in claim 1 comprising operating said magnetic resonance scanner to acquire said raw data from the examination subject by executing a pulse sequence that comprises B1 insensitive RF pulses.

12. An image correction device for correcting magnetic resonance image data, comprising:
   a computer comprising an input interface that receives an electronic designation of a representative reception profile that represents a reception profile of a reception antenna arrangement of a magnetic resonance scanner;
   said computer being configured to determine a correction function that corrects an asymmetry of said representative reception profile with respect to a symmetry plane of an examination subject from whom magnetic resonance raw data will be acquired with said magnetic resonance scanner;
   said computer being configured to operate the magnetic resonance scanner to acquire magnetic resonance raw data from the examination subject;
   said computer being configured to apply a reconstruction algorithm to said raw data to reconstruct image data therefrom, said image data comprising intensity values that are distorted due to said asymmetry of the representative reception profile with respect to said symmetry plane of the examination subject; and
   said computer being configured to specifically correct said distortion of said intensity values of said image data caused by the representative reception profile being asymmetric with respect to the symmetry plane of the examination subject, by multiplying the intensity values of the image data with said correction function, and thereby obtaining corrected image data, and to make the corrected image data available from the computer in electronic form as a data file.

13. A magnetic resonance apparatus comprising:
   a magnetic resonance scanner comprising a reception antenna arrangement;
   a computer provided with an electronic designation of a representative reception profile that represents a reception profile of a reception antenna arrangement of a magnetic resonance scanner;
   said computer being configured to determine a correction function that corrects an asymmetry of said representative reception profile with respect to a symmetry plane of an examination subject from whom magnetic resonance raw data will be acquired with said magnetic resonance scanner;
   said computer being configured to operate the magnetic resonance scanner to acquire magnetic resonance raw data from the examination subject;
   said computer being configured to apply a reconstruction algorithm to said raw data to reconstruct image data therefrom, said image data comprising intensity values that are distorted due to said asymmetry of the representative reception profile with respect to said symmetry plane of the examination subject; and said computer being configured to specifically correct said distortion of said intensity values of said image data caused by the representative reception profile being asymmetric with respect to the symmetry plane of the examination subject, by multiplying the intensity values of the image data with said correction function, and thereby obtaining corrected image data, and to make the corrected image data available from the computer in electronic form as a data file.

14. A non-transitory, computer-readable data storage medium encoded with programming instructions, said data storage medium being loaded into a control computer of a magnetic resonance apparatus that comprises a magnetic resonance scanner with a reception coil arrangement, said programming instructions causing said control computer to:

receive an electronic designation of a representative reception profile that represents a reception profile of a reception antenna arrangement of a magnetic resonance scanner;

determine a correction function that corrects an asymmetry of said representative reception profile with respect to a symmetry plane of an examination subject from whom magnetic resonance raw data will be acquired with said magnetic resonance scanner;

operate the magnetic resonance scanner to acquire magnetic resonance raw data from the examination subject;

apply a reconstruction algorithm to said raw data to reconstruct image data therefrom, said image data comprising intensity values that are distorted due to said asymmetry of the representative reception profile with respect to said symmetry plane of the examination subject; and specifically correct said distortion of said intensity values of said image data caused by the representative reception profile being asymmetric with respect to the symmetry plane of the examination subject, by multiplying the intensity values of the image data with said correction function, and thereby obtaining corrected image data, and to make the corrected image data available from the computer in electronic form as a data file.

* * * * *